United States Patent
Eltorai et al.

(10) Patent No.: US 11,204,598 B2
(45) Date of Patent: Dec. 21, 2021

(54) MEDICAL AND SURGICAL PROCEDURE TRAINING SYSTEM

(71) Applicant: Orthopedix, Inc., Louisville, KY (US)

(72) Inventors: Adam E. M. Eltorai, Louisville, KY (US); Ashok Seetharam, Louisville, KY (US); Lee E. Rubin, Louisville, KY (US)

( * ) Notice: Subject to any disclaimer, the term of this patent is extended or adjusted under 35 U.S.C. 154(b) by 0 days.

(21) Appl. No.: 16/020,382

(22) Filed: Jun. 27, 2018

(65) Prior Publication Data
US 2020/0004224 A1   Jan. 2, 2020

(51) Int. Cl.
G06T 17/00   (2006.01)
G05B 19/4099   (2006.01)
G16H 30/20   (2018.01)
G06F 16/903   (2019.01)

(52) U.S. Cl.
CPC ... G05B 19/4099 (2013.01); G06F 16/90335 (2019.01); G16H 30/20 (2018.01); G05B 2219/49023 (2013.01)

(58) Field of Classification Search
CPC ......... G06T 17/20; G06T 19/00; G06T 17/00; G06T 17/10; G06T 17/005
USPC ....................................................... 345/420
See application file for complete search history.

(56) References Cited

U.S. PATENT DOCUMENTS

| | | | | |
|---|---|---|---|---|
| 2009/0311655 A1* | 12/2009 | Karkanias | ............... | G09B 23/28 434/262 |
| 2010/0099066 A1* | 4/2010 | Mire | ....................... | G09B 23/34 434/272 |
| 2012/0035888 A1* | 2/2012 | Shin | ........................ | G06T 17/00 703/1 |
| 2014/0324469 A1* | 10/2014 | Reiner | ................... | G16H 50/20 705/3 |
| 2016/0259899 A1* | 9/2016 | Ludviksson | ........... | G16H 50/20 |
| 2017/0270709 A1* | 9/2017 | Tran | ........................ | A43B 13/04 |
| 2018/0329609 A1* | 11/2018 | De Swarte | .............. | G06T 19/00 |

OTHER PUBLICATIONS

Vebtola,. C.L., Medical Applications for 3D Printing:Current and Projected Uses, P&T, Oct. 2014, vol. 39 No. 10, [online],[Retrieved on Sep. 12, 2019], Retrieved from the Internet: <URL: https://pdfs.semanticscholar.org/add4/18d3bf363a0d5f60e38ced61cc82058168d2.pdf?_ga=2.242304320.35673681 (Year: 2014).*

* cited by examiner

*Primary Examiner* — Gordon G Liu
(74) *Attorney, Agent, or Firm* — Armis IP Law, LLC

(57) ABSTRACT

A system and apparatus for selection and fabrication of surgical models allows a database of files of anatomical systems and regions with specific anatomy, pathology, and severity for a corresponding specific surgical model fabrication. A database stores files with data for fabrication of 3D models arranged by anatomical system, ailment or disease, severity, region and location, for allowing selection of a model appropriate to instructional subject matter desired, such as surgical procedure training on unique anatomy and pathology. A server employs a GUI for user selection for narrowing and identifying parameters for the model. An interface to a manufacturing machine, such as a 3D or additive printer to produce the surgical model using materials approximating the emulated tissues. Additionally, the fabricated models include integrated attachment components to fasten and orient the model to a surface for surgical training instrumentation.

14 Claims, 6 Drawing Sheets

MEDICAL AND SURGICAL PROCEDURE TRAINING SYSTEM

BACKGROUND

Hands-on training is a significant aspect of surgical, medical, and veterinary procedure training and research. Training models have been developed for their realistic haptic feedback to avoid the problems associated with traditional use of cadaveric specimens. However, such models are limited in their breadth of anatomic and pathologic variation.

Trainees encounter patients with anatomy or pathology that may be uncommon or having aspects never before seen or managed. This new patient's anatomy or pathology presents unique procedural considerations, which warrant additional preparation. Without procedural models representative of the anatomy/pathology variation, the trainee would be limited in their ability to adequately prepare for the particular case.

Simulation models that resemble the breadth of anatomical/pathological variation that may be observed in practice would be of benefit to surgical, medical, and veterinary procedural trainees.

SUMMARY

A system and apparatus for selection and fabrication of surgical models allows a database of anatomical systems and regions to be queried based on an ailment for treatment, and a surgical model rendered via 3D (3-Dimensional) printing for fabricating a realistic instructional appliance or model for student activity. A database stores data for fabrication of 3D models arranged by anatomical system, ailment or disease, region and location, for allowing selection of a model appropriate to instructional subject matter desired. A server employs a GUI for user selection to narrow and identify parameters for the fabricated model. An interface to a 3D printer or additive manufacturing capability renders the surgical model using materials approximating the emulated tissue and bone structures. Additional models are re-creatable as needed to provide availability of instructionally matched specimens for trainee use. A comprehensive range of anatomical attributes may be represented and rendered as a fabricated model for teaching use, applicable to a variety of trainees such as medical students, researchers and testers.

Configurations herein are based, in part, on the observation that educational processes for medical education and research often rely on medical and biological supply houses for obtaining experimental specimens for surgical practices. Unfortunately, conventional approaches to obtaining realistic and accurate surgical models for trainee and instructional use are often limited by availability of cadaver donors or closely approximated animal specimens. Synthetic replicas may be available from medical supply vendors, but are typically offered only for a limited range of anatomical structures, and must be ordered, shipped, and delivered prior to use. Accordingly, configurations herein substantially overcome the shortcomings of conventional medical specimen channels by providing an "on demand" fabrication database of anatomy and pathological variation, and fabrication methods via 3D printing and/or additive manufacturing techniques. The result is a comprehensive library of models, covering a breadth of anatomic and/or pathologic variations that are printable on-demand and then ready for procedural/surgical training quickly. Integrated clamp-like attachments enable realistic procedural manipulation and forces to be applied by positioning and biasing the model as if anatomically attached. In contrast to conventional approaches, anatomical parameters are selectable, including an anatomical system, region, orientation, shape of the desired model, along with selectable properties emulating clinical conditions such as bone density, disease severity and complexity. Conventional approaches to anatomical or surgical based teaching aids involve mass production of models with predetermined, immutable characteristics, not on-demand individual model fabrication based on user selectable characteristics.

A server responsive to a GUI retrieves user selected 3D renderable form such as an STL or similar print format. Renderable database images are gathered from a variety of sources for conversion to a renderable form in the database. Print mediums are selected to approximate the texture and characteristics of the replicated anatomical systems, providing a realistic and recreatable surgical model for student and experimental use.

In further detail, the method of fabricating surgical models for medical surgical, or veterinary training and research as disclosed herein includes receiving a request for a surgical model, in which the request includes an anatomical system, region and pathology, and identifying, in a database of anatomical models, a scan corresponding to the request. The database is built from sanitized (anonymous and/or public domain) scans of patient data, and cataloged according to a depicted ailment or dysfunction exhibited by the scan. Individual scans may be aggregated or combined with others from, the anatomical system and/or region (i.e. skeletal wrist) to generate more comprehensive e models. Users, such as medical students and instructors, employ a GUI for navigating the database using the cataloged parameters to identify one or more scans, and generate, based on the identified scan, a 3D (3-dimensional) file indicative of a surgical replica of the anatomic system and region, and having the received ailment or healthy indicators. A 3D printer or additive manufacturing capability then renders a physical model of the generated surgical replica.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example of a surgical model fabrication apparatus and method for maintaining a database of scan data (scans) of anatomical systems, regions and ailments of varying degrees of compromise, a GUI (Graphical User Interface) for navigating and selecting scan data to incorporate into the final model, and a printer or additive manufacturing capability for rendering (printing) the completed surgical model.

Any suitable rendering approach may be employed. While 3-Dimensional (3D) printing and additive manufacturing techniques are deemed most applicable to the digital scan files, rendering may be performed by either additive manufacturing or non-additive. A rendering apparatus such as a 3D printer allows on-site or remote production of the model, which is preferred given the uniqueness of the models. Alternatively, for users without 3D rendering capability, the model may be produced remotely and then delivered to the user for use, in response to remote/web-based GUI access.

Figure 1:
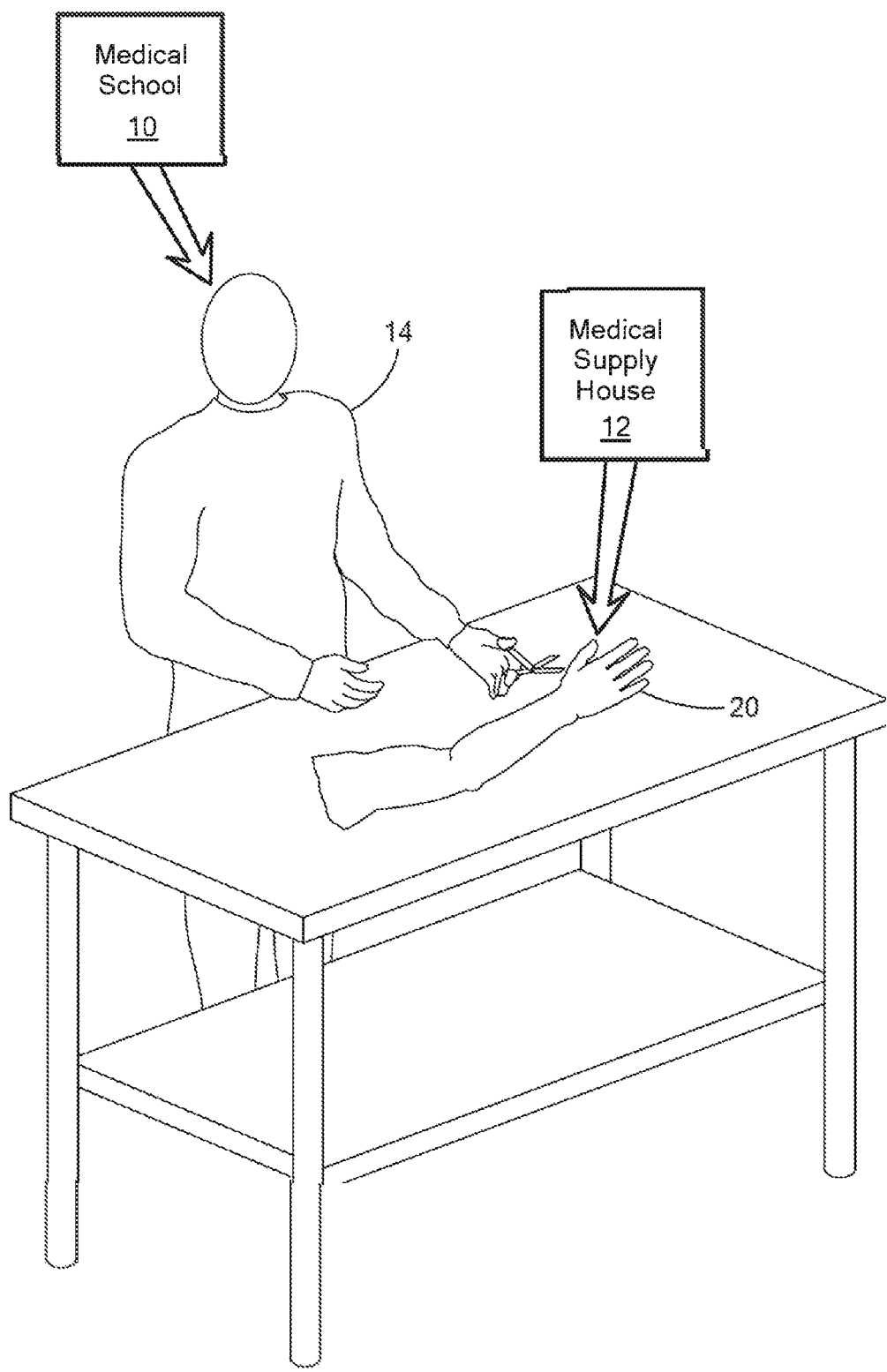
FIG. 1 is a context diagram including prior art practices.

FIG. 1 is a context diagram including prior art practices delivering predetermined, static molds. Referring to FIG. 1, conventional instructional tools used by a medical school 10 are often supplied by a medical supply house 12 or other vendors. Physical models and specimens of animals for dissection are commercially available through these channels. A medical student 14 or other user can obtain a mass produced simulated limb 20 or other experimental specimen for instruction and training on medical procedures. However, such conventional simulated limbs 20 are available only for a small number of samples, with little or no variation available. It may be difficult to find a conventional simulated limb or other sample that is well suited to a particular instructional task. Further, such simulated anatomy is often depicted in ideal health, and does not exhibit any diseased condition which may be the subject of instruction.

Figure 2:
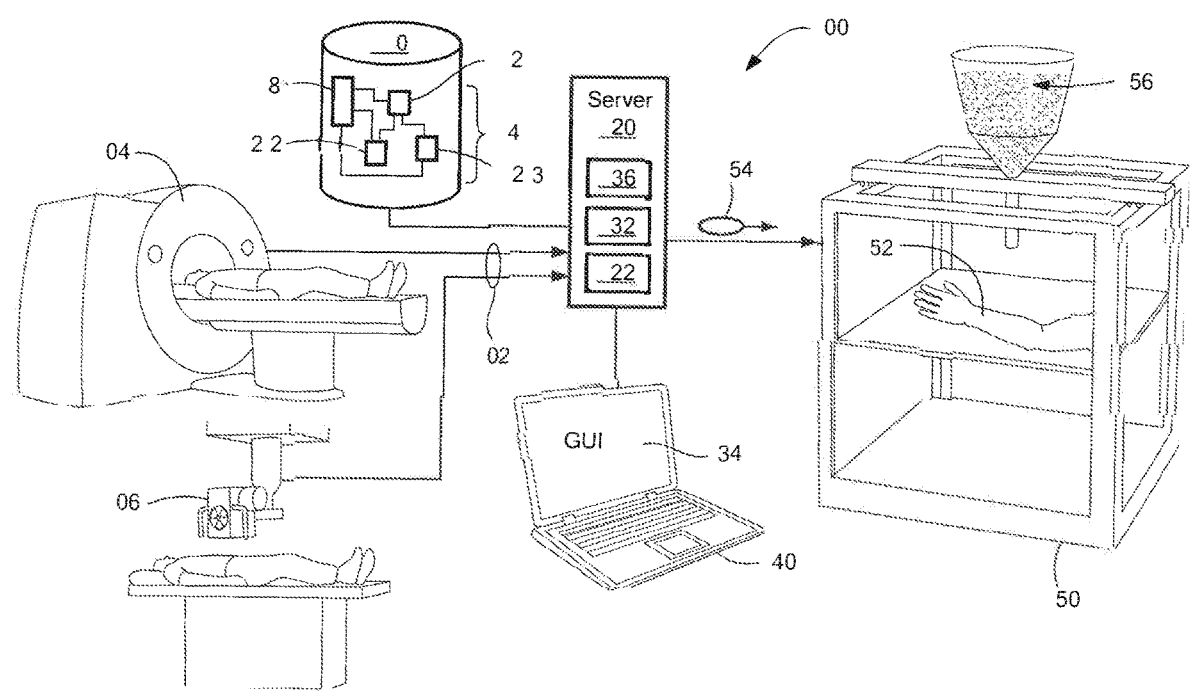
FIG. 2 is a block diagram of teaching appliance fabrication as disclosed herein.

FIG. 2 is a block diagram of teaching appliance fabrication as disclosed herein. Referring to FIG. 2, in a medical teaching and instructional environment 100, scan data 102 emanates from multiple sources, such as CT/MRI scanners 104 and X-ray machines 106. A storage device 110 or other storage medium receives a plurality of scans 112-1 ... 112-3 (112 generally), such that each of the scans includes graphical data resulting from genericized image scans of a patient. An intake process catalogs each of the scans 112 according to anatomical system, region, ailment and severity, resulting in an database 114 having an organized hierarchy 114 of scans 112, and indexed and arranged via a catalog 118. An anatomic variance may also be applied, similar to severity, to further subdivide different scans of the same anatomy. Upon building a number of stored scans, the storage device 110 accumulates a library of surgical models for depicting an anatomical system, a region or structure of interest, and a disease or diagnosis that is the subject of an academic undertaking.

A server 120 includes an intake process 122 for cataloging the gathered scans 112, and a selection application (app) 132 for selecting scans 112 for printing/rendering. A user device 140, which may be a laptop, desktop, or other suitable computing device, is responsive to the selection app 132 via a GUI 134. The selection app 132 generates a hierarchical GUI 134 navigable by anatomical system, region, ailment and severity, and is operable to receive navigation input for traversing among available scans 112 in the database 114 based on the navigation input. Upon selection by a user 14, a 3D printer 150 renders a completed surgical model 152 for surgical use, demonstration and instruction.

Figure 3:
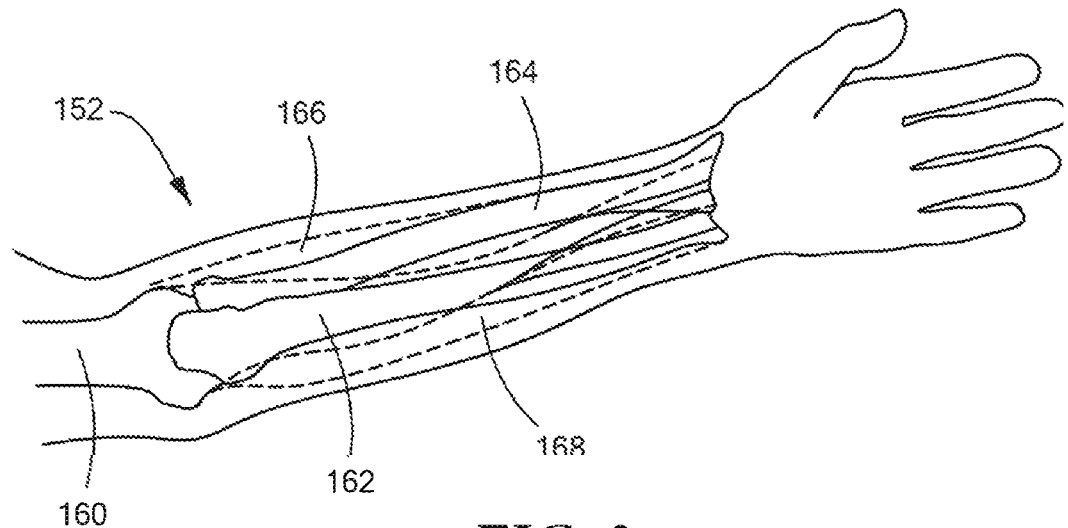
FIG. 3 is a teaching appliance or model fabricated using the approach disclosed herein.

FIG. 3 is a teaching appliance or model 152 fabricated using the approach disclosed herein. Referring to FIGS. 2 and 3, the server 120 includes a transformation and rendering application 136 for 3D printing based on the selected scans 112. Upon user selection, the rendering application converts the scan data into an STL rendering file 154 or other format representing a physical rendering medium, and sends the rendering file 154 to the printer 150 to generate the model 152. Depending on the print medium material, the printer 150 renders the operable surgical model 152 in a resilient form responsive to surgical tools and surgical attachment structures. The print medium material 156 approximates the natural bone and tissue of the anatomical structure it corresponds to. For example, a print medium may include cobalt chromium alloy to emulate a bone. Skeletal structures are hard, and rigid, while muscle depictions are flexible and responsive to needles and connective means such as sutures. Selection of a print medium may be stored with the scans, and emulates the physical properties of the anatomical systems represented.

In particular, the print mediums are selected based on the following criteria:
manufacturability;
resemblance to the characteristics of patient tissues;
individual materials may be used or combination of materials;
may involve post-production processing;
materials may be from organic materials, such as bio-printing; and
materials may be synthetic, such as polymers.

For example, a model 152 of an appendage depicting an arm might be represented by rigid, simulated bone medium for the humerus 160, radius 162 and ulna 164. The musculature may be represented by a more resilient print medium for the flexor carpi ulnaris 166 and flexor carpi radialis 168. Further, not all anatomical structures need be represented or printed in a particular model. Individual components, such as certain bones or muscles, may be omitted to illustrate otherwise obscured members.

Figure 4:
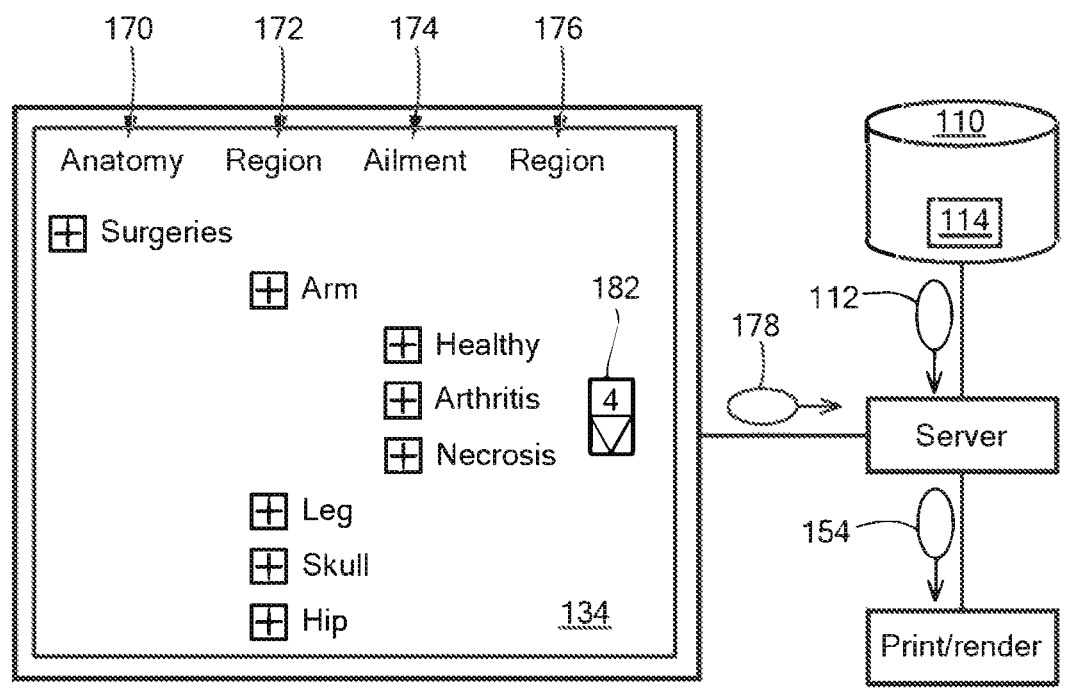
FIG. 4 is a GUI data flow diagram including a database supporting the approach herein.

FIG. 4 is a GUI data flow diagram including a database supporting the approach herein. Referring to FIGS. 2 and 4, the selection app 132 presents a GUI 134 for selecting the data on which the model 152 is based by denoting scan 112 or scans to be converted and printed. The GUI 134, in the example arrangement, allows selection of an anatomical system 170, region 172, ailment 174 and severity or degree 176. The anatomical system 170 defines the bodily function depicted by the model, such as skeletal, vascular, nervous, muscular, epidermal, digestive, to name several. A region 172 defines the area of the body concerned, such as appendages, torso or skull regions of the skeletal system. Certain systems may denote the region, such as a digestive system model would likely be based on the abdominal region. Ailment 174 defines the symptom, disease or condition exhibited, if other than normal, healthy anatomy. Skeletal members may experience necrosis, arthritis or fractures, for example. Similarly, the ailment may also define the region, as with an occluded valve denoting the heart. Also, a severity 176 may be specified, for conditions having degrees of degradation or progression. The severity 176 also provides for an anatomic variance between different scans. Medical ailments are often described in terms of degrees or stages indicating the progression of symptoms or compromise. This selection allows models depicting various degrees of disease progression. For example, an advanced bone disease may warrant a print medium that results in a more brittle bone model. Any suitable GUI features may be employed, such as expansions, buttons, pull-downs, and the like for guiding the user through a selection.

The example shown depicts a hierarchical expansion of these categories, however any suitable selection menu may be employed. Since certain ailments may only affect particular regions or systems, selection of an ailment may be the optimal first selection. In contrast to conventional approaches, surgical models 152 are selectable based on a focused anatomical system and location, and based on a particular disease (or lack thereof), and multiple models 152 may be generated to illustrate the progression of the same area, or a common ailment affecting different regions. In the case of a particular disease or condition, the selection app 132 renders a graphical user interface 134 indicative of a disease severity of the selected ailments, and receives an indication of the disease severity, shown as pulldown 182. The rendering app 136 retrieves, from the database 114, a scan 112 depicting the received disease severity for the relevant ailment and anatomical system.

Upon GUI identification by the user 14, the selection 178 passes to the server 120 to retrieve the scan data. The database 114 is arranged by anatomical systems, regions, ailments and a degree of disease state, to correspond to the selection app 132. The server 120 interrogates the database 114 to retrieve relevant scans 112, and the scans 112 are passed to the rendering application 136 for conversion to an STL file 154 and 3D printing.

The scans 112, defined by anatomy/pathology files may be from real patients or synthetic or a modified scan. Radiographic scans may serve as the basis for the digital models. Also, the digital model may be synthetic and designed for certain characteristics. The resulting generated model results from modified scan combining patient and designed models. Further, each file adds to the library, creating a continuous distribution of characteristics, varying in every dimension.

A particular advantage is exhibited by ailments affecting a plurality of anatomical systems. For example, a bone (skeletal) condition that is remedied by connective alterations to the musculature affects two anatomical systems. In such a case, the selection app 132 identifies each of the anatomical systems affected by the ailment and retrieves scans 112 based on each of the anatomical systems concerned, for the appropriate regions and ailments. The rendering application 136 renders the operable surgical model 152 including a material composition based on each respective anatomical system, skeletal and musculature, in this case.

Further, the database 114 may supplement or augment images by employing contralateral images where appropriate. If a corresponding scan of an opposed body side (right/left) is available where the desired side is not, a contralateral imaging approach is applied to the scan to generate a reverse, or mirror image model. Many structures are disposed on opposed sides, i.e. left and right sides. Configurations herein transpose and interpolate a structure from an opposed side scan to approximate the model of the desired side.

Figure 5:
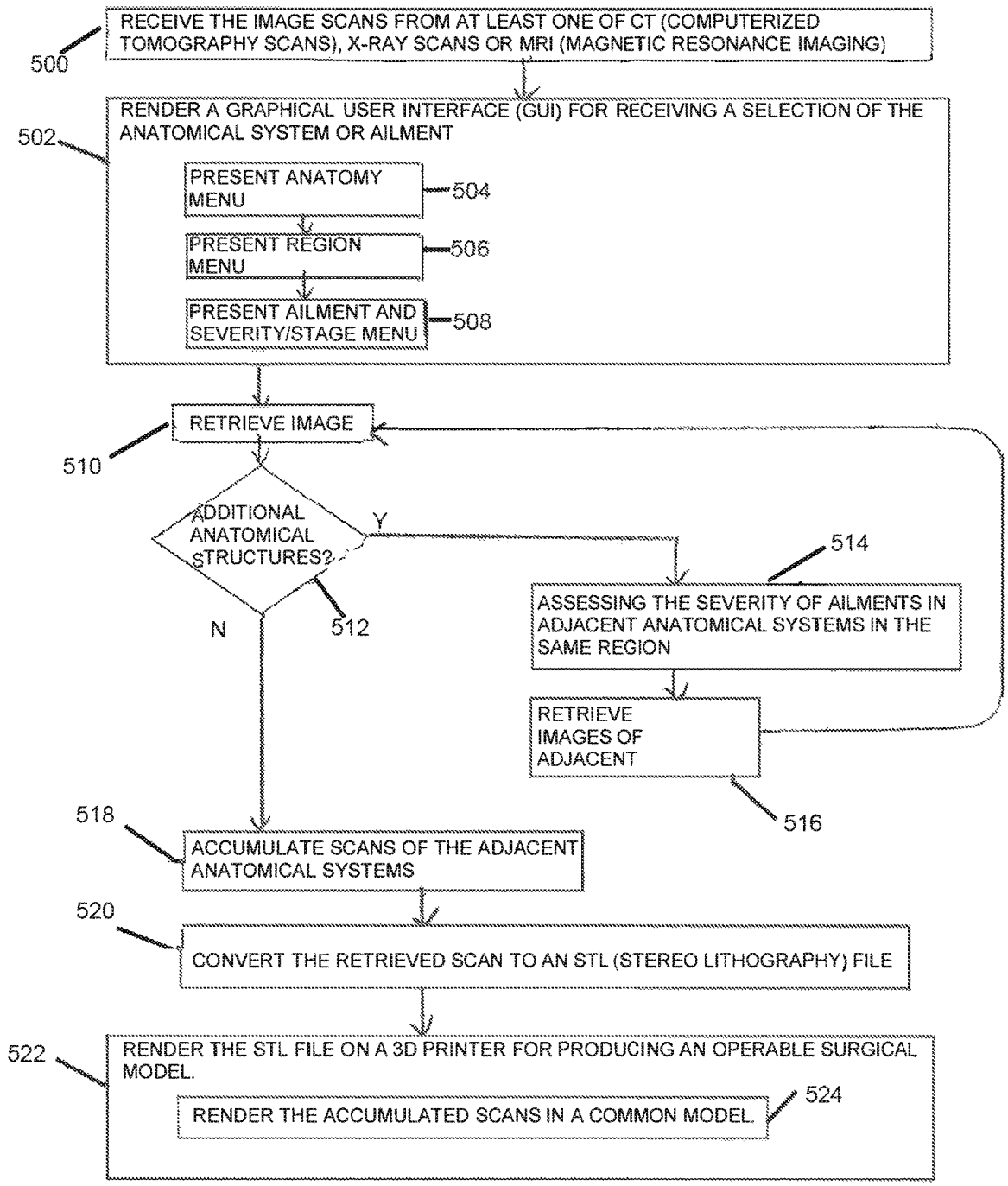
FIG. 5 is a flowchart of selection of a surgical model for rendering according to the data flow of FIG. 4.

FIG. 5 is a flowchart of selection of a surgical model for rendering according to the data flow of FIG. 4. Referring to FIGS. 2, 4 and 5, at step 500, the database 114 receives the image scans 112 via the intake app 122 from at least one of CT (Computerized Tomography scans), x-ray scans or MRI (Magnetic Resonance Imaging), however any suitable imaging technology may be employed. Scans 112 are gathered from clinical executions of the scan apparatus on actual patients, and the personal patient data sanitized so that the stored scan 112 is anonymous with only symptomatic information. No personal data regarding the patient is saved.

Upon achieving a minimal quantum of scans 112, the selection app 132 renders a graphical user interface (GUI) for receiving a selection of the anatomical system or ailment affecting the anatomical system, as shown at step 502. This includes presenting the anatomy 170 menu, at step 504, the region 172 at step 506, and the ailment 174 and severity 176 menu at step 508. In operation, any suitable selection interface may be employed—the selection need not be done in a rigid hierarchy. Receiving the request may include rendering a graphical user interface (GUI) for receiving a selection of the ailment, and identifying, from the ailment, the affected anatomical system as the anatomical system of the request, as in an ailment that affects a single organ or location. The selection identified by the app 132 will be used to select one or more scans 112 based on the anatomy, region, ailment and degree parameters of the selection. It may occur that a scan depicting the exact parameters or severity is unavailable. In such an instance, multiple similar scans may be coalesced to approximate the desired attributes. For example, if a particular skeletal structure is sought for moderate necrosis, and the only scans available include mild and severe necrosis, the available scans may be combined and coalesced to approximate the attributes of a moderate necrosis.

The rendering app 136 retrieves the image data representing the scan 112 from the database 114, as depicted at step 510. In particular configurations, multiple scans may be coalesced. In this instance, a check is performed, at step 512, to identify additional anatomical structures for consideration. The selection app 122 assesses the severity of ailments in adjacent anatomical systems in the same region, as depicted at step 514, and retrieves scans 112 of adjacent or related regions or systems, as shown at step 516. An adjacent anatomical region might be, for example, muscles adjacent skeletal members, or arteries and nerves running alongside a skeletal member. After retrieving any additional images by accumulating scans of the adjacent anatomical systems, as shown at step 518, the rendering application 136 converts the retrieved scan to an STL (Stereo Lithography) file, as shown at step 520. Other suitable 3D rendering representations may also be employed. Rendering app 136 then instructs the printer 150 to render the STL file on a 3D printer for producing the operable surgical model 152, as shown at step 522. In the case of multiple scans 112, this includes rendering the accumulated scans in a common model 152, as depicted at step 524.

FIGS. 6A-6D depict a user interface for selection of a surgical model having attributes based on selections from the database. FIGS. 6A-6D show an example GUI for selecting additional attributes to be applied to the surgical replica. In addition to the anatomical system and ailment, attributes such as bone density, orientation and shape are selectable and applied to the rendered physical model by applying the attributes to a 3D printed rendering of the physical model. Depending on the anatomical model selected, other attributes may be applicable. The user interface applies the attributes to a parameter selection to match against the anatomical models available. The example presented shows a GUI sequence for selecting and coding/indexing the anatomical structure and a severity of an ailment, however other approaches to identifying appropriate scans for trainee use may be employed. In the example shown, an indexing syntax codes the attributes for database reference, and may also help identify surgical replicas which differ by subtle or non-visible attributes, such as bone density.

Figure 6A:
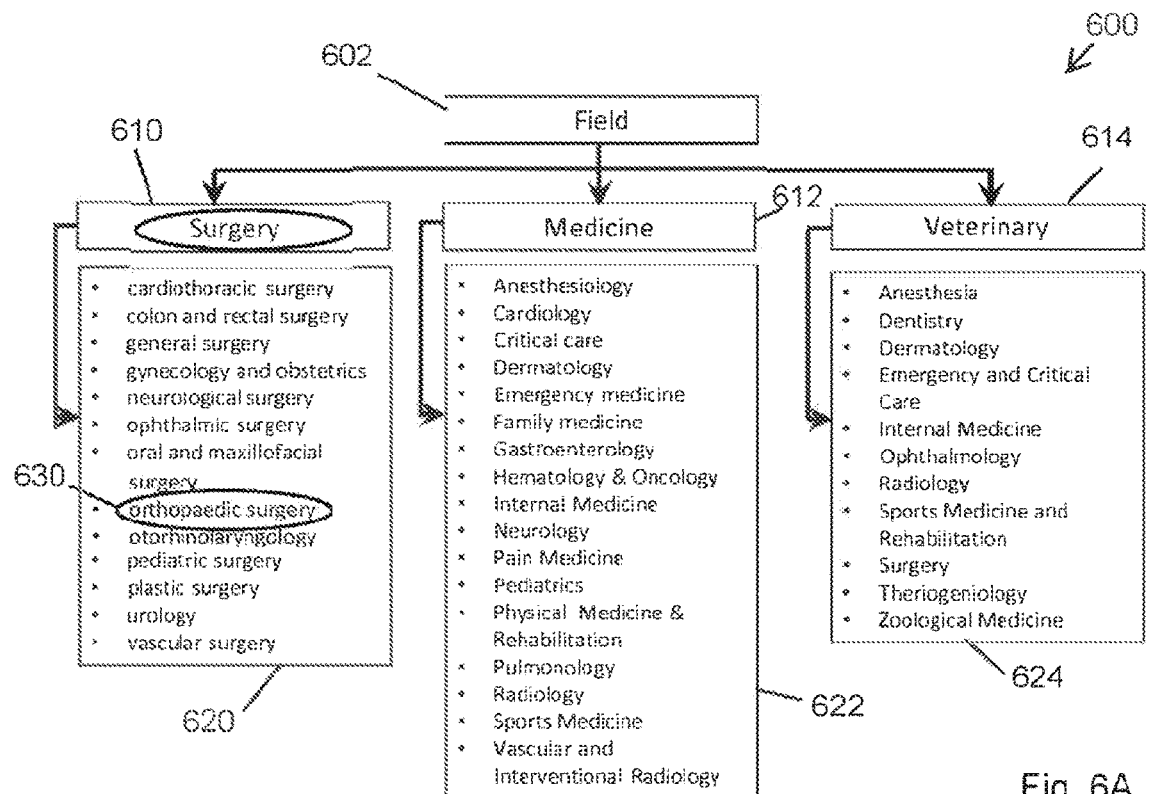
FIGS. 6A-6D depict a user interface for selection of a surgical model having attributes based on selections from the database.
Figure 6B:
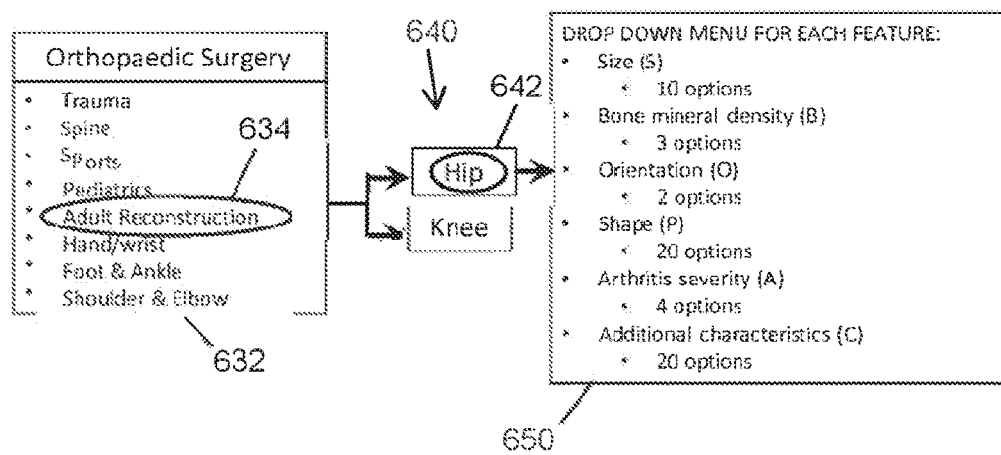

FIG. 6A shows a menu selection tree 600 for selecting a field 602 from among surgery 610, medicine 612 and veterinary sciences 614. Within each medical field are a set of procedure areas 620, 622 and 624, respectively. A user clicks on a selected procedure area 630 to continue. Control progresses to FIG. 6B. Within the selected procedure area, a set of available procedures 632 leads to a procedure selection 634 and region 640 selection 642.

Figure 6C:
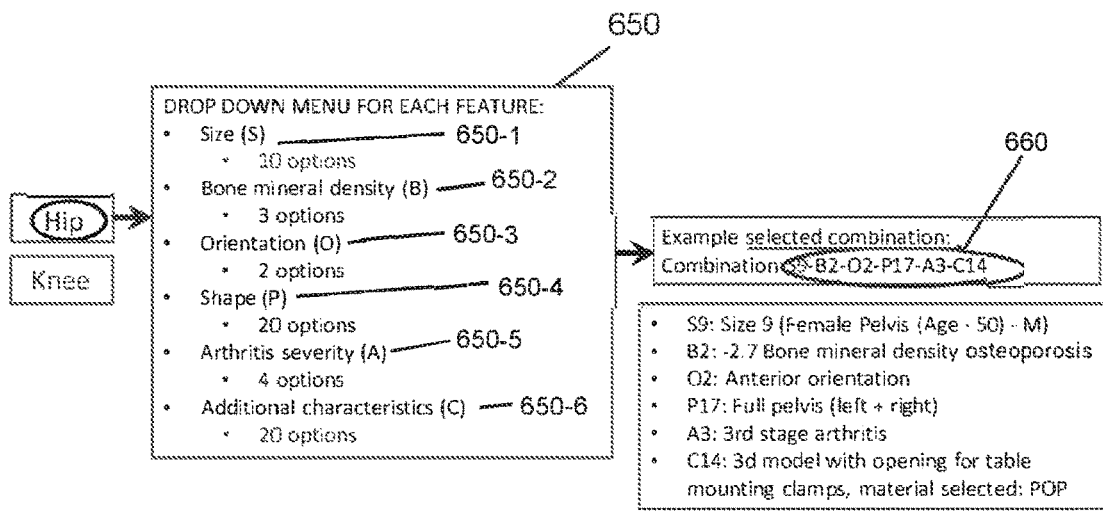
Figure 6D:
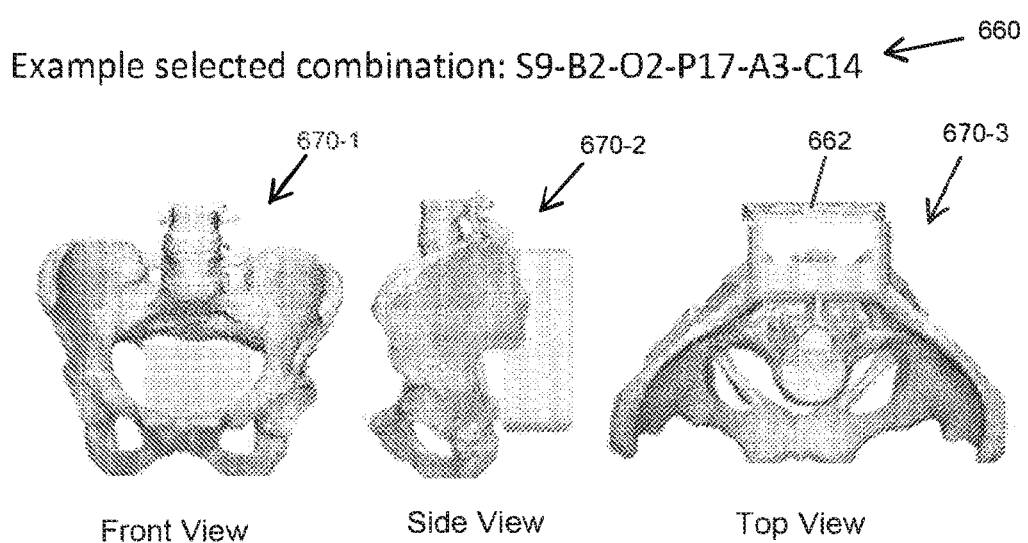

A set of attributes 650 available for the selected procedure 634 allows selection of particular attributes along with a corresponding designator 650-1 . . . 650-6, as shown in FIG. 6C. Each designator 650-N also has a value indicative of an available range, magnitude or degree. Each attribute therefore includes a designator and a value, such that the designator defines a property of the physical model and the value is indicative of a degree of the property. The value is a suffix to the designator 650-N, and the set of selected attributes form a combination 660 of attributes applicable to the particular rendered physical model.

A beneficial feature of the user interface allows the user to select the desired model characteristics with a combination of various characteristics. The characteristics may reflect a never before seen anatomy or pathology, by selecting a combination of attributes that are unlikely or impossible to occur naturally. Individual files that meet those characteristics are used for model fabrication, or alternatively, new files are produced to meet the specifications of the desired characteristics.

Rendering involves indexing scan information in the database based on the attributes, and coalescing the selected attributes in the rendered surgical replica. Based on the attributes selected in the GUI, the server 120 indexes the scans based on the designator and the value and retrieves the identified scans. The server 120 then coalesces a plurality of the identified scans for approximating the received request based on matching the received attributes to parameters of the scans. For example, a bone density attribute is satisfied by a print medium having the proper characteristics. A size attribute can be satisfied by scaling the scan data. For attributes such as shape, it is preferable if the database has scans of each shape option. If a particular shape option is not available, the attribute could be satisfied by a combination of scans that approximate the desired shape. The resulting surgical replica is shown in a plurality of views 670-1, 670-2 and 670-3 in FIG. 6D. A clamping plate 662 or appendage may be selected by the orientation attribute, which provides a flush surface for clamping the surgical replica in the position desired for surgery.

The clamping plate 662 is a protrusion, appendage, bracket or planar extension that is integrated into and/or fabricated with the surgical replica.670. The clamping plate 662 may take a variety of positions on the same surgical replica 670 to allow for clamped positioning in different orientations. This is selectable from an orientation attribute on the GUI. Conventional approaches employ replicas or models curvatures and shapes that are difficult and awkward to clamp into different positions on a tabletop. By having a secure molded clamping region that is flat (planar) or otherwise designed to mate with clamping or holding apparatus, a secure tabletop model is provided which can be rendered for clamping in a variety of positions.

The available clamped orientations allow for realistic force from instrumentation (e.g., drilling, reaming) to be applied to the models. This is beneficial for realistic haptic feedback and practice. The orientation defines a frame of reference and rotation of the generated surgical replica to allow for access to a surgically manipulated area. Such an integrated clamp-like apparatus may be readily built-in into the model, thus reducing a need for separate attachment fixtures to firmly secure the surgical replica 670. From the identifying an orientation of the surgical model, the rendered attachment extends from the rendered physical model based on the identified orientation, such that the attachment is adapted for fixation on a work surface from a clamping force, adhesion, or brace to prevent rolling, for example. Integrated attachments are printed or rendered into or onto the surgical model. The is beneficial when applying pressure to the model during instrumentation, such that the model may be fastened to a surface (table). In particular configurations, integrated into the model is a fastening system, or alternately, alternatively, integrated into the model is a surface or opening onto which an additional fastening system may attach. Such a fastening system may include a clamp protrusion, elongated surface, or void (such as a hole or hook) that is engageable by any suitable fastener such as a screw, clamp, bolt, etc. The attachment is therefore engageable with the fastener(s) for securement to the work surface at an angle defined by the orientation, the orientation selected based on a region of surgical interest on the surgical replica.

Those skilled in the art should readily appreciate that the programs and methods defined herein are deliverable to a user processing and rendering device in many forms, including but not limited to a) information permanently stored on non-writeable storage media such as ROM devices, b) information alterably stored on writable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method of fabricating surgical models for medical training, comprising:
   receiving a request for a surgical model, the request including an anatomical system, region and ailment receiving the request further comprising:
     rendering a graphical user interface (GUI) for receiving a selection of the ailment; and
     identifying, from the ailment, the affected anatomical system as the anatomical system of the request;
   identifying, in a database of anatomical models, at least one file corresponding to the request;
   generating, based on the identified file, a 3D (3-dimensional) surgical replica of the anatomic system and region, and having the received ailment;
   receiving a set of attributes based on the ailment, the attributes affecting a renderable parameter of the surgical replica; and rendering a physical model of the generated surgical replica;
wherein the ailment affects a plurality of anatomical systems, further comprising:
identifying each of the anatomical systems affected by the ailment;
retrieving scans based on the anatomical systems; and
rendering the operable surgical model including a material composition based on each respective anatomical system, the material composition selected based on at least one of manufacturability, polymer characteristics and organic characteristics.

2. The method of claim 1 further comprising arranging the database by anatomical systems, regions, ailments and a degree or complexity of disease state.

3. The method of claim 2, further comprising:
determining that a contralateral mirror image file of a desired scan or file exists in the database;
retrieving the contralateral mirror image file from the database; and
employing the contralateral mirror image file to transpose and interpolate satisfying the request, such as a model for a left hip from a right hip file.

4. The method of claim 1 further comprising:
assessing the severity of ailments in adjacent anatomical systems in the same region;
accumulating files or scans of the adjacent anatomical systems; and
rendering the accumulated files or scans in a common model.

5. The method of claim 1 wherein the anatomical systems include skeletal, vascular, nervous, muscular, epidermal, or digestive.

6. The method of claim 1 further comprising:
identifying an orientation of the surgical replica; and
rendering an attachment extending from the surgical replica based on the identified orientation, the attachment adapted for fixation on a work surface.

7. The method of claim 1 further comprising:
receiving, from the GUI, an indication of an orientation, the orientation defining a frame of reference and rotation of the generated surgical replica; and
generating a clamp protrusion, attachment site, fastener, or other fixation component on the physical model based on the received orientation.

8. A method of fabricating surgical models for medical training, comprising:
receiving a request for a surgical model, the request including an anatomical system, region and ailment
receiving the request further comprising:
rendering a graphical user interface (GUI) for receiving a selection of the ailment; and
identifying, from the ailment, the affected anatomical system as the anatomical system of the request;
identifying, in a database of anatomical models, at least one file corresponding to the request;
generating, based on the identified file, a 3D (3-dimensional) surgical replica of the anatomic system and region, and having the received ailment;
receiving a set of attributes based on the ailment, the attributes affecting a renderable parameter of the surgical replica; and
rendering a physical model of the generated surgical replica;
generating a hierarchical GUI navigable by anatomical system, region, ailment and severity;
receiving navigation input for traversing among available scans in the database based on the navigation input; and
selecting a plurality of scans or files for combination, each of the scans selected based on at least one of anatomical systems, regions, ailments and a degree or complexity of disease state.

9. The method of claim 8 further comprising applying the attributes to a 3D printed rendering of the physical model.

10. The method of claim 9 wherein the attributes include a designator and a value, the designator defining a property of the physical model and the value indicative of a degree of the property.

11. The method of claim 10 further comprising:
indexing the scans or files based on the designator and the value;
retrieving the scans or files; and
coalescing a plurality of the scans or files for approximating the received request based on matching the received attributes to parameters of the scans or files.

12. A database of anatomical models, comprising:
a plurality of scans and files resulting from gathered patient data or fabricated 3D models;
a catalog of the scans and files, the catalog defining, for each scan or file of the plurality of scans and files, an anatomical system, region, ailment and severity, the catalog further responsive for:
identifying each of the anatomical systems affected by the ailment; and
retrieving scans or files based on the anatomical systems for rendering the operable surgical model including a material composition based on each respective anatomical system; and
an interface to a selection application, the interface operable to receive a request including parameters defining a scan or file for retrieval, the parameters defining an anatomical system, region, ailment and severity,
the interface responsive to a rendering application for transmitting, based on a correspondence between the request parameters and the catalog, a selected scan or file to the rendering application for conversion and rendering as a physical, 3D surgical model; and
the interface further responsive to determine that a contralateral file or scan of a desired side of the body exists in the database, and to retrieve the contralateral scan or file from the database for employing the contralateral scan or file to transpose and interpolate a scan or file satisfying the correct-side request.

13. A computer program product on a computer readable storage medium having instructions that, when executed by a processor, perform a method of fabricating a surgical model for medical training, the method comprising receiving a request for a surgical model, the request including an anatomical system, region and ailment;
identifying, in a database of anatomical models, at least one scan corresponding to the request, the database arranged by anatomical systems, regions, ailments and a degree of disease state;
generating, based on the identified scan, a 3D (3-dimensional) file indicative of a surgical replica of the anatomic system and region depicted in the scan;
receiving a set of attributes based on the ailment, the attributes affecting a renderable parameter of the surgical replica, wherein the set of attributes includes a designator and a value, the designator defining a property of the physical model and the value indicative of a degree of the property;

indexing the scans or files based on the designator and the value;

retrieving the identified scans or files; and coalescing a plurality of the identified scans or files for approximating the received request based on matching the received attributes to parameters of the scans or files;

applying the attributes to a 3D printed rendering of the physical model, wherein the attributes include a designator and a value, the designator defining a property of the physical model and the value indicative of a degree of the property; and rendering a physical model of the generated surgical replica.

14. The computer program of claim 13 wherein the database is responsive to:

receiving a plurality of scans or files, each of the scans or file including graphical data resulting from genericized image scans of a patient or fabricated files; and cataloging each of the scans and files according to anatomical system, region, ailment and severity.

\* \* \* \* \*